United States Patent
Nemeth

(10) Patent No.: US 6,224,662 B1
(45) Date of Patent: May 1, 2001

(54) USE OF NOVEL GLASS COMPOSITIONS IN PREPARING DENTAL GLASS PILLARS AND SUPPORT PILLARS, AND METHOD FOR PRODUCING THE GLASS PILLARS

(76) Inventor: Laszlo Nemeth, 9400 Sopron, Madach u.5. (HU)

( * ) Notice: Subject to any disclaimer, the term of this patent is extended or adjusted under 35 U.S.C. 154(b) by 0 days.

(21) Appl. No.: 09/230,045
(22) PCT Filed: Jul. 19, 1996
(86) PCT No.: PCT/HU96/00040
 § 371 Date: Jan. 19, 1999
 § 102(e) Date: Jan. 19, 1999
(87) PCT Pub. No.: WO98/03146
 PCT Pub. Date: Jan. 29, 1998
(51) Int. Cl.[7] ............................. A61K 6/02; C03C 3/091; C03C 4/00; A61C 13/00
(52) U.S. Cl. ................. 106/35; 433/201.2; 433/220; 433/202.1; 433/212.1; 501/66; 65/63; 65/64; 65/102
(58) Field of Search .................. 501/66; 106/35; 65/102, 63, 64; 433/201.1, 202.1, 212.1, 220

(56) References Cited

U.S. PATENT DOCUMENTS

| | | | |
|---|---|---|---|
| 4,215,033 | * 7/1980 | Bowen | 106/35 |
| 4,481,036 | * 11/1984 | Panzera | 501/66 |
| 4,515,634 | * 5/1985 | Wu et al. | 106/35 |
| 4,744,759 | * 5/1988 | Bowen | 106/35 |
| 6,090,194 | * 7/2000 | Brodkin et al. | 106/35 |

FOREIGN PATENT DOCUMENTS

| | | |
|---|---|---|
| 4323143 | * 12/1994 | (DE) . |
| 332887 | * 9/1989 | (EP) . |

OTHER PUBLICATIONS

Derwent Abstract 94–061906 for JP 6–16,452, dated Jan. 25, 1994.*

* cited by examiner

Primary Examiner—C. Melissa Koslow
(74) Attorney, Agent, or Firm—Browdy and Neimark

(57) ABSTRACT

The present invention relates to the use of novel glass compositions in preparing dental glass pillars and support pillars, and method for producing the glass pillars. The glass material comprises a high percent of boron trioxide which makes possible a reduced alkali oxide content. The dental glass pillars thus obtained are bio-compatible and can be used in the preparation of dental bridgework, most preferably when posterior teeth serving for support of the said bridgework are missing.

4 Claims, 3 Drawing Sheets

USE OF NOVEL GLASS COMPOSITIONS IN PREPARING DENTAL GLASS PILLARS AND SUPPORT PILLARS, AND METHOD FOR PRODUCING THE GLASS PILLARS

TECHNICAL FIELD

The present invention relates to the use of novel glass compositions in preparing dental glass pillars and support pillars, and method for producing the glass pillars.

BACKGROUND ART

Missing teeth disturb the perfect locking of dentition and the harmony of chewing. Neglecting these strongly influences somatic and mental harmony. Loss of molar teeth is most frequent which can be substituted initially by inserting bridgework. However, building in fixed bridgework can be impeded by loss of the posterior tooth supporting the row end. This problem can be solved only by removable prosthesis. Insufficient chewing due to lack of substitute teeth can adversely influence gastric and intestinal functions. Aesthetical look of visage is also altered, which can cause psychical disorders.

Several methods for substitution of teeth are known, including among others, methods providing special dental bridgework with fixed or with non-fixed end, the use of which can raise problems well known in the art.

Hungarian patent 210.237 granted on Nov. 1, 1994 relates to substitution of missing posterior teeth by metal bridgework provided with glass stump and a method to make the said metal bridgework. The dental bridge according to the above patent includes a conventional metal bridge body and one or more glass stump(s) attached to the metal bridge body with its (their) tapering end(s). The essence of the patent is, that the glass stump supporting the metal bridgework is formed from molten glass, and matches the shape of tooth saddle, and the glass stump, or, in case of several glass stumps, at least one of them is fastened to the terminal back element of the metal bridgework. When making the metal bridgework, a molten glass bar is pressed on the appropriate location of the model made by conventional method, followed by slowly cooling the glass mould corresponding to the shape of the saddle, after cooling, the sides opposite to the gums are ground and cut, the glass stump is temporarily fixed on the model and fixed in the metal bridgework previously prepared. A glass stump made from a glass crock by a German dentist already in 1936 was similar to the described means, but instead of melting, it was formed by grinding only.

According to the above referred Hungarian patent the glass bar was melted suitably at a temperature of 524 to 526° C. The suitable glass composition disclosed in the description was the following: 73.0% $SiO_2$, 7.0% $B_2O_3/As_2O_3/Al_2O_3$, 2.5–5% MgO and the rest being $ZnO/BaO/PbO/Fe_2O_3/Na_2O/K_2O$.

The durability of special dental bridges with non-fixed end can substantially be increased by using support pillar (possibly support pillars) conforming to the shape of the gums. A great number of requirements can be set as to the proprieties of the fastening element of circular or elliptical cross-section shape. The most important requirements are as follows:

a) appropriate rigidity to endure strains resulting from chewing, long-term resistance against chemical reactions occurring in the mouth, b) long-term tissue tolerance and inactivity when used in human organism, c) appropriate softening characteristics for use in dental laboratory conditions, and subsequent plasticity so that its structure remains inactive, and its rigidity be maintained under chewing load as well.

According to experiences, particularly inorganic glasses meet these requirements. However, due to their composition, most glasses are not suitable for dental purposes, as they do not meet the above requirements. Some other glasses can be used only by compromises. Therefore, there is the need to provide a glass of special composition meeting most suitably the described conditions of use. It was the aim of the present invention to work out such a glass of special composition.

The so-called support pillar, provided as support of the free end of the dental bridgework must have a substantial mechanical resistance to endure the generally known high pressing and shearing forces occurring while chewing even when considering the altered distribution of stress compared to conventionally fixed dental bridgeworks. Unstrained silicate glass seems to be suitable for this purpose, its modulus of elasticity being usually in the interval from 500 to 800 mPa, and its compressive strength is high compared to conventional plastic materials.

The Mohs hardness of 5 to 7 of this glass is sufficiently high to make support pillars which would not be scratched by food. Namely, surface micro-scratches play an important role in breaking. Surface micro-scratches would deteriorate mechanical properties as well. Such glass shows high resistance to abrasion as well, although in the application according to the invention it is obviously not exposed to as intensive erosion as the teeth.

The thermal and electrical conductivity of glass is low. There is no danger that glass forms a galvanic cell in the mouth, and accelerates corrosion of parts made from other metals and built in the mouth.

Preferably the structural material to be inserted should possess chemical resistance. Silicate glasses usually meet this requirement. However, the composite reaction between glasses and solutions contacting the glasses such as saliva, should be considered. Such reactions can be basically separated in two processes being in interaction with each other. As a result of the first process, hydrogen ions are passing on the glass surface from the solution, penetrating by slow diffusion in the interior of the glass. Concurrently, alkaline ions, particularly sodium ions are passing in the solution in an amount equivalent with the hydrogen ions. This partial process makes the solution alkaline. The second process results in slow degradation of the polymer structure of glass during which all elements constituting the glass, go in solution. Both processes take place usually slowly at normal body temperatures, however, velocity can greatly alter according to the glass composition. In a disadvantageous case, a substantial local increase of pH and/or dissolving of toxic materials harmful for the organisation must be taken into account.

The selection of the structure material and the simplicity of the technology to be used, are also important factors, i.e. the support pillar could be formed and fastened in the bridge in customary dental mechanic's laboratories easily and in short time. From this point of view the dental glass pillar is particularly advantageous. The glass pillar of the invention can be simply heated up to the proper temperature, then pressed on the appropriate location of the plaster model, preferably using a tool designed for this purpose, and is cooled regularly to avoid unfavourable stresses. The above mentioned Hungarian patent does not meet all the above requirements.

DESCRIPTION OF DRAWINGS

The invention will be explained further below with reference to the accompanying drawings, wherein.

DISCLOSURE OF THE INVENTION

Figure 1:
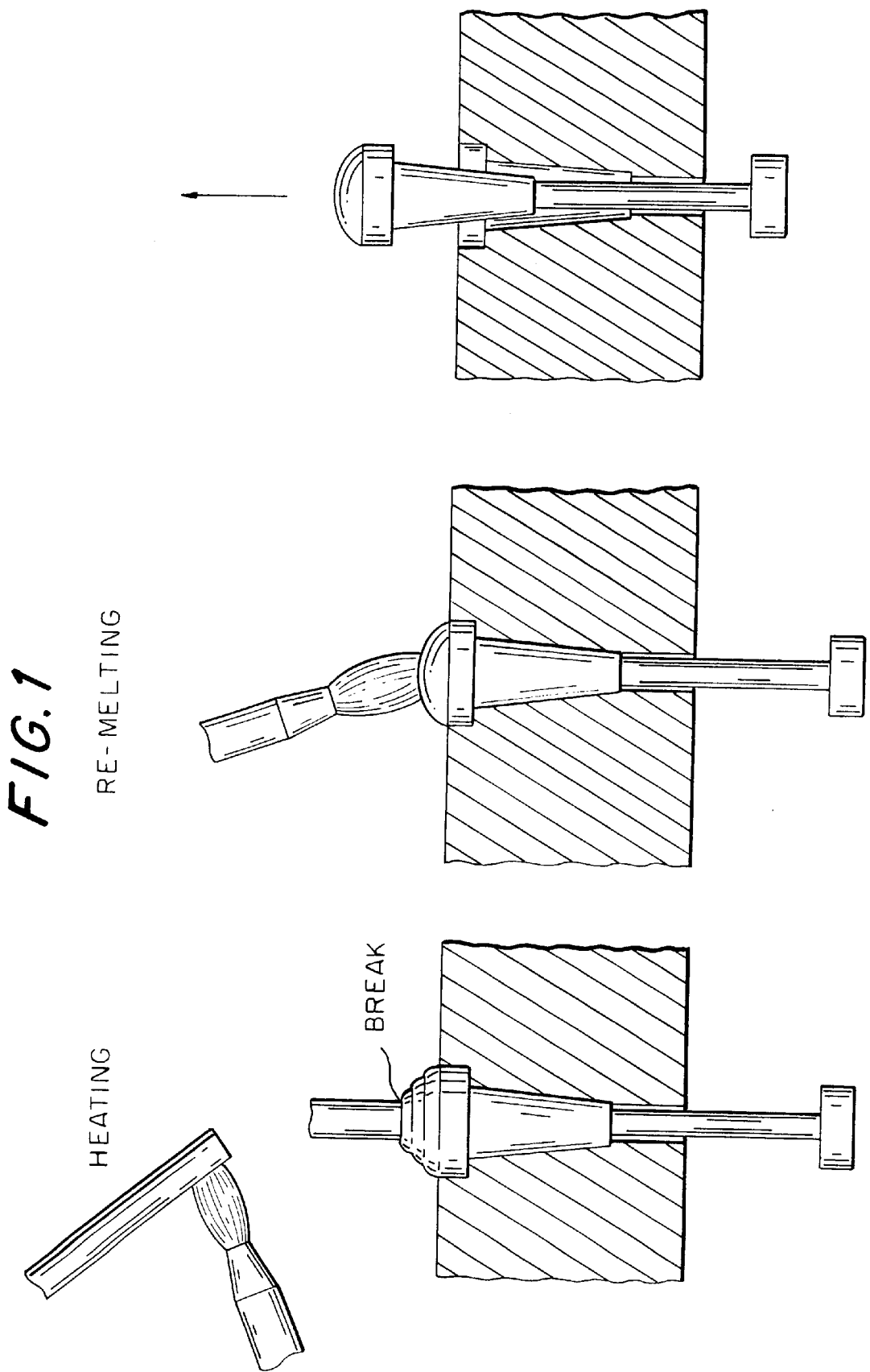
FIG. 1 shows the manufacturing process of the preformed glass pillar product used for making the support pillar.

One object of the present invention is to provide a fully bio-compatible material, which can also be prepared commercially so that the physical and chemical characteristics of all parts of the product constantly meet the above main requirements.

This object is achieved, according to the invention, by a glass composition having the following constitution:

| silica | $SiO_2$ | 70–75% |
|---|---|---|
| boron trioxide | $B_2O_3$ | 12–18% |
| sodium oxide | $Na_2O$ | 4–8% |
| potassium oxide | $K_2O$ | 0.5–2.0% |
| aluminium oxide | $Al_2O_3$ | 0.8–2%. |

Physical characteristics of the material are as follows:

The glass material is melted in a furnace at 1560–1600° C.

The working temperature: 1400° C.

Linear expansion coefficient: $4–4.2.10^{-6}K^{-1}$.

Compression strength: 120–150 mPa.

Acid resistance: hydrolytic class I.

Base resistance: hydrolytic class II.

When examining the composition it was stated that, besides the main components, it can include insignificant amounts of zinc and magnesium as accompanying impurities (Zn 0.01% and MgO 0.006%), which remain, however, inactive and unable to effect irritation and health damage. The composition does not contain lead or barium which are harmful to health.

Softening temperature is sufficiently low enabling to form the material by heat sources available in dental mechanic's laboratory. This advantageous property is due to the high borate content, which makes possible the reduction of the otherwise indispensable high alkali content. Reducing the concentration of sodium oxide influences the chemical resistance of the glass very advantageously. On the one hand the low alkali content is advantageous as the amount of the materials passing from the glass by corrosion in the organism is small, and even the negligible amount of the dissolved components is non-toxic. On the other hand, it is advantageous, as due to the low sodium concentration, corrosion induces no essential increase of the pH-value near the gums.

Another object of the invention is the glass pillar made from the above glass composition, preferably appearing in a ready form suitable for use in dental mechanics.

According to the process disclosed in the previously mentioned Hungarian patent the glass stump is formed by pressing a glass bar on the model. The glass bar must be melted in relatively great length, and while pressing it on the model, the melted stump tends to deform in the longitudinal axis of the glass bar. Accordingly, the method is complicated, and without appropriate skill there is a risk of high reject rates.

The material composition and thereby the physical and chemical characteristics of the glass according to the present invention are constant, which provides an easy handling. The preferred way for producing and using of the glass according to the present invention will be explained in detail below:

Glass is molten from the stock material, the composition of which conforms to the above description, at 1580–1600° C., suitably in a furnace built and maintained for this purpose (in case of a furnace used for other purposes, parts remaining on the wall of the melting pot may produce undesirable contamination, therefore they are preferably to be removed), then 4 mm thick glass bars are drawn. The glass bars are cooled by directed cooling to avoid unfavourable stresses, as heated glasses, depending on material composition, react on outside temperature in different ways. In the glass according to the invention unfavourable stresses might arise during rapid cooling, therefore a controlled cooling temperature must be used in the stock material until cooling under 450° C.

The bars thus produced constitute the stock material for pillar manufacturing. The tools used for pillar manufacturing are the following: oxygen/propane gas heating burner, press mould containing the shape of pillar as shown on FIG. 1, pincers, and heat treating chamber or heat insulating mat for cooling the finished product according to the technology.

The preferred process of pillar manufacturing is the following: the previously manufactured glass bars are heated by means of the heating burner to 900–1200° C., and are pressed onto form in the press mould preheated to 600–700° C. and maintained steadily at 600–700° C. by means of a separate burner. The press mould is preferably to be maintained at this temperature, as at higher temperatures the material can adhere to the tool, and at lower temperatures the product can be cooled too fast causing harmful stresses. After the glass adapted the shape of the press mould (about 1 second), it will be separated from the bar by means of flame, the pillar is removed from the press mould by means of the out-thrust mandrel, and placed in the heat treating chamber wherein it is gradually cooled to room temperature.

Subsequently the convex surface formed on the location of the separation is polished perpendicularly to the longitudinal axis by means of a diamond disc thereby promoting the future work of the dental technician.

The pillar thus obtained is ready for commercial marketing or direct use.

Figure 2:
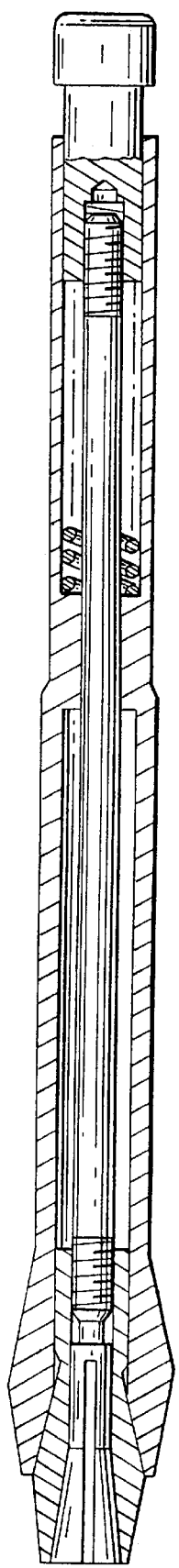
FIG. 2 is a cross-section of the special tool (fitting tool) used during applying of the glass pillar.
Figure 3:
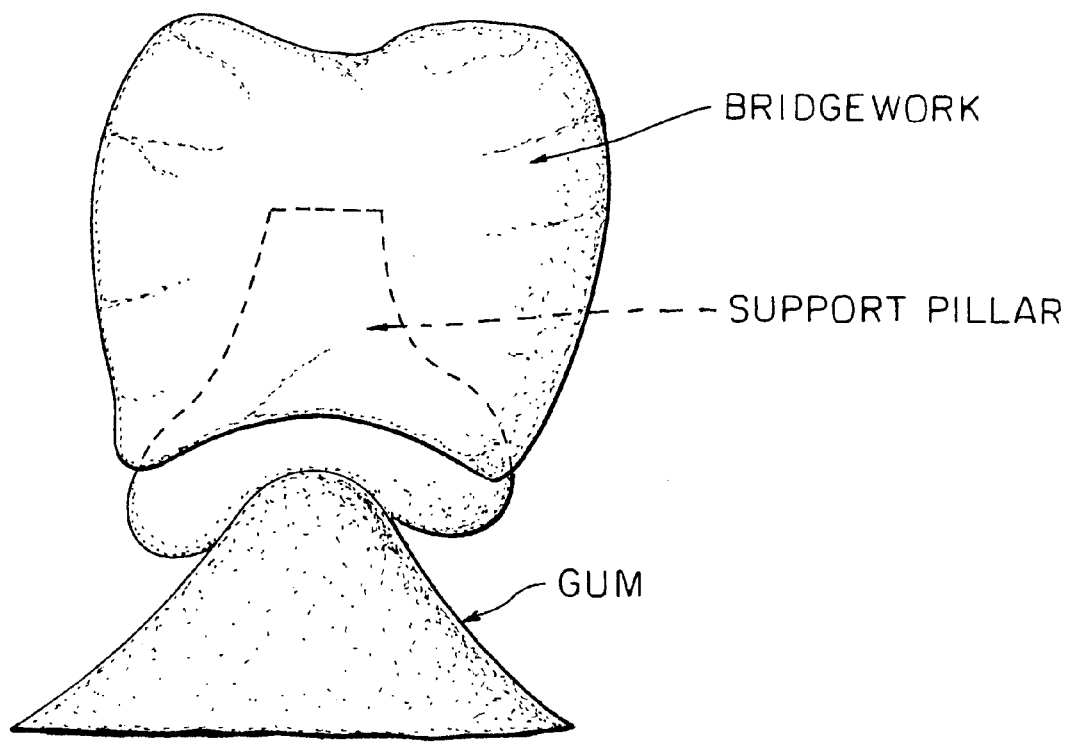
FIG. 3 shows the cross-section of a support pillar placed on the gum shaped according to the form thereof.

The use by dental technician to form the support pillars is accomplished as follows:

The glass pillar is placed in the clamp according to FIG. 2 and heated by oxygen/propane to white heat, a temperature of about 900 to 1200° C. until the material softens and becomes deformable.

The softened material is pressed by a firm movement directed perpendicularly to the web onto the location indicated on the prepared plaster model, subsequently its surface is repeatedly heated holding it over flame a short time, then dropped in and covered by ceramic mats where the support pillar prepared in the described manner cools uniformly in one step in its full mass at least under 450° C. thus avoiding harmful stresses on the pressed surface.

The end of the support pillar opposite to the pressed surface is formed conforming to the requirements of inserting in the bridgework by means of diamond cutter and diamond grinder currently used in glass industry. The support pillar prepared in this way is treated to conform the pillar teeth on the model and fixed in the finished bridgework by means of cement bond.

The support pillars manufactured from the glass according to the invention and/or the support pillars according to the invention were used on about 150 patients, by performing periodical macro-examinations, X-ray controls, and, if it was possible examining the fixed and later removed dental bridge. No pathological changes could be observed neither in the environment beneath the support pillar, nor in the neighbouring environment. Comparing the X-ray panorama photographs taken before and after the work, the bone contours beneath the support pillar and the last pillar tooth were the same.

What is claimed is:

1. A dental structure formed of glass of the following composition:

| silica | $SiO_2$ | 70–75% |
|---|---|---|
| boron trioxide | $B_2O_3$ | 12–18% |
| sodium oxide | $Na_2O$ | 4–8% |
| potassium oxide | $K_2O$ | 0.5–2.0% |
| aluminium oxide | $Al_2O_3$ | 0.8–2%. |

2. The dental structure of claim 1 in the form of a glass pillar suitable for providing a bio-compatible dental support pillar.

3. In a method of preparing a support pillar for hidden or unhidden dental bridgeworks, wherein said pillar is formed of glass, the improvement wherein said glass has the following composition:

| silica | $SiO_2$ | 70–75% |
|---|---|---|
| boron trioxide | $B_2O_3$ | 12–18% |
| sodium oxide | $Na_2O$ | 4–8% |
| potassium oxide | $K_2O$ | 0.5–2.0% |
| aluminium oxide | $Al_2O_3$ | 0.8–2%. |

4. A process for producing a glass pillar for providing a bio-compatible dental support pillar, comprising:

heating a glass composition to a temperature of 900–1200° C., said glass composition comprising:

| silica | $SiO_2$ | 70–75% |
|---|---|---|
| boron trioxide | $B_2O_3$ | 12–18% |
| sodium oxide | $Na_2O$ | 4–8% |
| potassium oxide | $K_2O$ | 0.5–2.0% |
| aluminum oxide | $Al_2O_3$ | 0.8–2%, | pressing said heated glass composition to shape in a press mold, and then continuously cooling said glass in one step to room temperature.

* * * * *